United States Patent
Ecke

(10) Patent No.: US 9,941,540 B2
(45) Date of Patent: Apr. 10, 2018

(54) COMPOSITE ELECTROLYTE FOR A SOLID OXIDE FUEL CELL, EXHAUST GAS PROBE OR HIGH-TEMPERATURE GAS SENSOR

(71) Applicant: Airbus Defence and Space GmbH, Ottobrunn (DE)

(72) Inventor: Christian Ecke, Rosenheim (DE)

(73) Assignee: AIRBUS DEFENCE AND SPACE GMBH, Taufkirchen (DE)

( * ) Notice: Subject to any disclaimer, the term of this patent is extended or adjusted under 35 U.S.C. 154(b) by 154 days.

(21) Appl. No.: 14/972,937

(22) Filed: Dec. 17, 2015

(65) Prior Publication Data

US 2016/0181646 A1    Jun. 23, 2016

(30) Foreign Application Priority Data

Dec. 19, 2014 (DE) .................. 10 2014 019 259

(51) Int. Cl.

| | |
|---|---|
| *H01M 8/12* | (2016.01) |
| *H01M 8/04* | (2016.01) |
| *G01N 27/407* | (2006.01) |
| *B29C 35/00* | (2006.01) |
| *H01M 8/1253* | (2016.01) |
| *C04B 35/488* | (2006.01) |
| *H01M 8/124* | (2016.01) |
| *B29L 31/34* | (2006.01) |

(52) U.S. Cl.
CPC ........... *H01M 8/1253* (2013.01); *B29C 35/00* (2013.01); *C04B 35/4885* (2013.01); *G01N 27/4073* (2013.01); *B29L 2031/3468* (2013.01); *C04B 2235/3206* (2013.01); *C04B 2235/3224* (2013.01); *C04B 2235/3225* (2013.01); *C04B 2235/3229* (2013.01); *C04B 2235/3246* (2013.01); *C04B 2235/5436* (2013.01); *C04B 2235/5454* (2013.01); *C04B 2235/6567* (2013.01); *C04B 2235/77* (2013.01); *H01M 2008/1293* (2013.01); *H01M 2300/0077* (2013.01); *H01M 2300/0091* (2013.01); *Y02E 60/525* (2013.01); *Y02P 70/56* (2015.11)

(58) Field of Classification Search
CPC ........ H01M 8/02; H01M 8/12; H01M 8/1253; H01M 8/10; H01M 8/124; B29C 35/00; G01N 27/4073

See application file for complete search history.

(56) References Cited

U.S. PATENT DOCUMENTS

| | | | | |
|---|---|---|---|---|
| 5,240,786 | A * | 8/1993 | Ong ................... | H01M 8/0271 29/623.2 |
| 5,580,673 | A * | 12/1996 | Farooque ............ | H01M 8/0295 29/623.5 |
| 2005/0089740 | A1* | 4/2005 | Moon ................. | H01M 4/8621 429/425 |
| 2005/0214616 | A1 | 9/2005 | Kumar et al. | |
| 2006/0125157 | A1* | 6/2006 | Swartzlander ........ | C04B 35/488 264/618 |
| 2007/0179041 | A1 | 8/2007 | Muroi et al. | |
| 2008/0193803 | A1* | 8/2008 | Sholklapper ........ | H01M 4/8621 429/482 |
| 2010/0112408 | A1* | 5/2010 | Yang ................... | C01G 25/006 429/489 |
| 2010/0167170 | A1 | 7/2010 | Narendar et al. | |
| 2013/0052562 | A1* | 2/2013 | Yoon ................... | H01M 8/126 429/489 |

FOREIGN PATENT DOCUMENTS

| | | |
|---|---|---|
| DE | 10212966 A1 | 10/2003 |
| DE | 10308747 A1 | 9/2004 |
| JP | 2009104990 A | 5/2009 |

OTHER PUBLICATIONS

German Patent Office, German Office Action for German Patent Application No. 10 2014 019 259.8 dated Oct. 22, 2015.
European Patent Office, European Extended Search Report for European Patent Application No. 15199985.1 dated Apr. 11, 2016.

* cited by examiner

*Primary Examiner* — Kenneth J Douyette
(74) *Attorney, Agent, or Firm* — Lorenz & Kopf, LLP

(57) ABSTRACT

This relates to a sinterable composite electrolyte compound, a sintered composite electrolyte, a method for manufacturing a sintered composite electrolyte and the use of the sintered composite electrolyte in a fuel cell, preferably a solid oxide fuel cell, an exhaust gas probe or a high-temperature gas sensor, and a fuel cell, preferably a solid oxide fuel cell, exhaust gas probe or high-temperature gas sensor containing the sintered composite electrolyte.

14 Claims, No Drawings

COMPOSITE ELECTROLYTE FOR A SOLID OXIDE FUEL CELL, EXHAUST GAS PROBE OR HIGH-TEMPERATURE GAS SENSOR

CROSS-REFERENCE TO RELATED APPLICATION

This application claims priority to German Patent Application No. 10 2014 019 259.8, filed Dec. 19, 2014, which is incorporated herein by reference in its entirety.

BACKGROUND

The present embodiment relates to a sinterable composite electrolyte compound, a sintered composite electrolyte, a method for producing a sintered composite electrolyte, and the use of the sintered composite electrolyte in a fuel cell, preferably a solid oxide fuel cell, an exhaust gas probe or a high-temperature gas sensor, and a fuel cell, preferably a solid oxide fuel cell, exhaust gas probe or high-temperature gas sensor containing the sintered composite electrolyte.

For reasons associated with the manufacturing process, an SOFC monobloc green body manufactured by Additive Layer Manufacturing (ALM) or non-conventional 3D manufacturing processes such as weaving technology must be produced directly from all required, electrochemically active layers. Accordingly, all of the layers or materials (anode, electrolyte, cathode), which may for example consist of three or as many as eight layers or materials, must be co-sintered at exactly the same temperature and for exactly the same bonding time. Since the materials become denser as the sintering temperature and bonding times increase, and remain more porous at lower temperatures, the need for a gas-impermeable electrolyte is in direct conflict with the need for electrodes having the highest possible degree of porosity. An electrolyte with a density greater than 5.90 g/cm$^3$ is considered gas-impermeable for the purposes of SOFC technology.

Thus, it would be desirable to provide a sinterable composite electrolyte compound that can be used for a fuel cell, preferably a solid oxide fuel cell, an exhaust gas probe or high-temperature gas sensor and has good ion-conducting capability ($O^{2-}$) in the sintered state. It would also be desirable to provide a sinterable composite electrolyte compound that can be processed by Additive Layer Manufacturing (ALM) or non-conventional 3D manufacturing processes such as weaving technology. Additionally, it would be desirable to create a sinterable composite electrolyte compound that still becomes gas-impermeable at sintering temperatures $T_{sinter} \leq 1300°$ C. and with a bonding time $t_{bond} < 5h$, yielding a sintered product having a density $\geq 5.9$ g/cm$^3$, which is also capable of thin dimensioning, i.e. has the highest possible mechanical stability.

The problem addressed by the present embodiment is therefore to provide a sinterable composite electrolyte compound that can be used for a fuel cell, preferably a solid oxide fuel cell, an exhaust gas probe or high-temperature gas sensor, and has good ion-conducting capability ($O^{2-}$) in the sintered state. This also addresses the further problem of ensuring that the sinterable composite electrolyte compound can be processed by Additive Layer Manufacturing (ALM) or non-conventional 3D manufacturing processes such as weaving technology. This also addresses the problem of ensuring that the sinterable composite electrolyte compound can be processed at sintering temperatures $T_{sinter} \leq 1300°$ C. and for a bonding time $t_{bond} < 5$ h and results in a gas-impermeable electrolyte composite that has a density $\geq 5.9$ g/cm$^3$ but at the same time is capable of thin dimensioning, i.e. has the highest possible mechanical stability.

These problems are solved with the objects defined in the claims. Advantageous embodiments are given in the dependent claims.

SUMMARY

A first object of the present embodiment is to provide a sinterable composite electrolyte compound, comprising an electrolyte selected from the group consisting of 8YSZ, 10Sc1CeSZ, 10Sc1A1SZ, 10Sc2YbSZ, 3YSZ, 6ScSZ and mixtures thereof, and at least one material distributed in the electrolyte in a quantity from 0.1 to 15.0% by weight relative to the total weight of the electrolyte, wherein the material has an average particle size $d_{50}$ from 1 to 80 nm.

The sinterable composite electrolyte compound can be processed by Additive Layer Manufacturing (ALM) or non-conventional 3D manufacturing processes such as weaving technology. A further advantage is that when sintered at sintering temperatures $T_{sinter} \leq 1300°$ C. and for a bonding time $t_{Bond} < 5$ h, the sinterable composite electrolyte compound yields an electrolyte composite that is gas-impermeable and has a density of $\geq 5.9$ g/cm$^3$ and at the same time lends itself to thin dimensioning. A further advantage is that the sinterable composite electrolyte compound according to the embodiment has good ion-conducting capability ($O^{2-}$) in the sintered state, and can consequently be used for a fuel cell, preferably a solid oxide fuel cell, exhaust gas probe or high-temperature gas sensor.

The sinterable composite electrolyte compound comprises the electrolyte in a quantity from 85 to 99.9% by weight relative to the total weight of the compound, for example.

The electrolyte has an average particle size $d_{50}$ from 0.5 to 5 μm, and/or the electrolyte has a particle size $d_{80} < 5$ μm, for example.

The at least one material distributed in the electrolyte material is selected from the group comprising 8YSZ, $Al_2O_3$, MgO, Al, Mg, 3YSZ, 6ScSZ, 10Sc1CeSZ, 10Sc1A1SZ, 10Sc2YbSZ and mixtures thereof, for example.

For example, the material distributed in the electrolyte comprises at least two materials selected from the group comprising 8YSZ, $Al_2O_3$, MgO, Al, Mg, 3YSZ, 6ScSZ, 10Sc1CeSZ, 10Sc1A1SZ, 10Sc2YbSZ and mixtures thereof preferably at least three materials selected from the group comprising 8YSZ, $Al_2O_3$, MgO, Al, Mg, 3YSZ, 6ScSZ, 10Sc1CeSZ, 10Sc1A1SZ, 10Sc2YbSZ and mixtures thereof.

For example, the sinterable composite electrolyte compound comprises the at least one material distributed in the electrolyte in a quantity from 0.2 to 10.0% by weight, relative to the total weight of the electrolyte.

For example, the at least one material distributed in the electrolyte has an average particle size $d_{50}$ from 2 to 50 nm.

For example, the at least one material distributed in the electrolyte is present in the form of nanopowder or nanofibres.

For example, the sinterable composite electrolyte compound also comprises a further material having an average particle size $d_{50}$ from 1 to 5 μm.

For example, the sinterable composite electrolyte compound comprises the additional material in a quantity from 0.1 to 1.0% by weight relative to the total weight of the electrolyte.

The present embodiment further provides a sintered composite electrolyte comprising the sinterable composite electrolyte compound, as described in the present document.

For example, the sintered composite electrolyte has a density of ≥5.9 g/cm³.

The present embodiment further provides a method for producing the sintered composite electrolyte, comprising the steps of preparing a sinterable composite electrolyte compound as described herein, and sintering the sinterable composite electrolyte compound at temperatures ≤1300° C. and for a bonding time <5 h.

The present embodiment also relates to the use of the sintered composite electrolytes, as described in the present document, in a fuel cell, preferably a solid oxide fuel cell, an exhaust gas probe or a high-temperature gas sensor. The embodiment further relates to a fuel cell, preferably a solid oxide fuel cell, an exhaust gas probe or a high-temperature gas sensor containing the sintered composite electrolyte as described herein.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

The present embodiment relates to a sinterable composite electrolyte compound comprising an electrolyte selected from the group consisting of 8YSZ, 10Sc1CeSZ, 10Sc1AlSZ, 10Sc2YbSZ, 3YSZ, 6ScSZ and mixtures thereof, and at least one material distributed in the electrolyte in a quantity from 0.1 to 15.0% by weight, relative to the total weight of the electrolyte, wherein the material has an average particle size $d_{50}$ from 1 to 80 nm.

The term "sinterable" means that fine-grained materials of metal and/or metal oxide are mixed and compacted at elevated temperature, wherein the temperatures remain below the melting temperature of the main component.

On requirement of the present embodiment is that the sinterable composite electrolyte compound comprise an electrolyte selected from the group consisting of 8YSZ, 10Sc1CeSZ, 10Sc1AlSZ, 10Sc2YbSZ, 3YSZ, 6ScSZ and mixtures thereof.

The electrolyte is the main component of the sinterable composite electrolyte compound.

In one embodiment, the sinterable composite electrolyte compound comprises 8YSZ, 10Sc1CeSZ, 10Sc1AlSZ or 10Sc2YbSZ, 3YSZ, 6ScSZ as the electrolyte. For example, the sinterable composite electrolyte compound comprises 8YSZ or 10Sc1CeSZ as the electrolyte. The sinterable composite electrolyte compound preferably comprises 10Sc1CeSZ as the electrolyte.

In one embodiment, the electrolyte is present in the cubic or tetragonal crystalline phase. The electrolyte is preferably present in the cubic crystalline phase.

In addition or alternatively thereto, the electrolyte exhibits sufficient mechanical stability. For example, the electrolyte exhibits mechanical stability in the order of 170 to 550 MPa or 170 to 350 MPa. The electrolyte preferably exhibits mechanical stability in the order of 180 to 250 MPa. Alternatively, the electrolyte exhibits mechanical stability in the order of 210 to 340 MPa.

In one embodiment, the electrolyte has a conductivity in the order of 0.07 to 0.25 S/cm or 0.07 to 0.23 S/cm. The electrolyte preferably has a conductivity in the order of 0.07 to 0.09 S/cm. Alternatively, the electrolyte has a conductivity in the order of 0.17 to 0.23 S/cm.

As was stated earlier, the electrolyte is the main component of the sinterable composite electrolyte compound. Accordingly, the sinterable composite electrolyte compound comprises the electrolyte in a quantity from 85 to 99.9% by weight relative to the total weight of the compound. Alternatively, the sinterable composite electrolyte compound comprises the electrolyte in a quantity from 90 to 99.9% by weight relative to the total weight of the compound. For example, the sinterable composite electrolyte compound comprises the electrolyte in a quantity from 90 to 95% by weight relative to the total weight of the compound.

In order to obtain a sinterable composite electrolyte compound with sufficient mechanical stability, it is advantageous if the electrolyte has a certain average particle size.

In particular, it is advantageous if the electrolyte has an average particle size $d_{50}$ from 0.5 to 5 μm. For example, the electrolyte has an average particle size $d_{50}$ from 0.7 to 2.5 μm. The electrolyte preferably has an average particle size $d_{50}$ from 0.9 to 1.5 μm.

Unless stated otherwise, all particle sizes were determined by laser scattering. Devices and methods for determining particle sizes by means of laser scattering are known to a person skilled in the art.

In addition or alternatively thereto, the electrolyte has a particle size $d_{80}$<5 μm.

In order to lower the sintering temperature of the sinterable composite electrolyte compound, it is a requirement of the present embodiment that the sinterable composite electrolyte compound contains at least one material distributed in the electrolyte in a quantity from 0.1 to 15.0% by weight relative to the total weight of the electrolyte, wherein the material has an average particle size $d_{50}$ from 1 to 80 nm.

It is particularly advantageous for the sinterable composite electrolyte compound if the at least one material distributed in the electrolyte is dispersed homogeneously therein.

Alternatively, the least one material distributed in the electrolyte may be dispersed inhomogeneously therein.

The least one material distributed in the electrolyte is preferably dispersed homogeneously in the electrolyte.

The sinterable composite electrolyte compound preferably comprises the at least one material distributed in the electrolyte in a quantity from 0.1 to 10.0% by weight, or from 0.1 to 7.5% by weight relative to the total weight of the electrolyte.

In principle, any material of metal and/or metal oxide that has an average particle size $d_{50}$ from 1 to 80 nm may be used. However, the at least one material distributed in the electrolyte is preferably selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof.

In one embodiment, the sinterable composite electrolyte compound contains a material distributed in the electrolyte that is selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof.

If the sinterable composite electrolyte compound is a material distributed in the electrolyte and selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof, the material distributed in the electrolyte is preferably 8YSZ.

Alternatively, the material distributed in the electrolyte contains at least two materials selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof. For example, the material distributed in the electrolyte comprises two materials selected from the group consisting of 8YSZ, $Al_2O_3$, MgO, Al, Mg, 3YSZ, 6ScSZ, 10Sc1CeSZ, 10Sc1AlSZ, 10Sc2YbSZ and mixtures thereof.

If the material distributed in the electrolyte comprises at least two, preferably two materials selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof, the material distributed in the electrolyte preferably comprises a mixture of MgO and $Al_2O_3$.

If the at least one material distributed in the electrolyte is present as a mixture of MgO and $Al_2O_3$, the mixture preferably comprises the mixture of MgO and $Al_2O_3$ in a certain weight ratio. For example, MgO and $Al_2O_3$ are present in a weight ratio (Wgt[MgO]/Wgt[$Al_2O_3$]) from 10:1 to 1:10. MgO and $Al_2O_3$ are preferably present in a weight ratio (Wgt[MgO]/Wgt[$Al_2O_3$]) from 5:1 to 1:5. In one embodiment, MgO and $Al_2O_3$ are present in a weight ratio (Wgt[MgO]/Wgt[$Al_2O_3$]) of approximately 1:1.

Alternatively, the material distributed in the electrolyte comprises at least three materials selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof. For example, the material distributed in the electrolyte comprises three materials selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof.

If the material distributed in the electrolyte comprises at least three, preferably three materials selected from the group comprising 8YSZ, $Al_2O_3$, MgO, Al, Mg, 3YSZ, 6ScSZ, 10Sc1CeSZ, 10Sc1AlSZ, 10Sc2YbSZ and mixtures thereof, the material distributed in the electrolyte preferably comprises a mixture of 8YSZ, $Al_2O_3$ and MgO.

If the at least one material distributed in the electrolyte is present as a mixture of 8YSZ, $Al_2O_3$ and MgO, the mixture preferably comprises 8YSZ, $Al_2O_3$ and MgO in a certain weight ratio. For example, 8YSZ, $Al_2O_3$ and MgO are present in a weight ratio (Wgt[8YSZ]/Wgt[$Al_2O_3$]/Wgt[MgO]) from 20:1:1 to 1:1:1. 8YSZ, $Al_2O_3$ and MgO are preferably present in a weight ratio (Wgt[8YSZ]/Wgt[$Al_2O_3$]/Wgt[MgO]) from 15:1:1 to 5:1:1. In one embodiment, 8YSZ, $Al_2O_3$ and MgO are present in a weight ratio (Wgt[8YSZ]/Wgt[$Al_2O_3$]/Wgt[MgO]) of approximately 10:1:1.

Therefore, the sinterable composite electrolyte compound comprises, preferably contains an electrolyte selected from the group consisting of 8YSZ, 10Sc1CeSZ, 10Sc1AlSZ, 10Sc2YbSZ, 3YSZ, 6ScSZ and mixtures thereof, and at least one, preferably at least two, even more preferably at least three, material/s distributed in the electrolyte in a quantity from 0.1 to 15.0% by weight relative to the total weight of the electrolyte, wherein the material/s has/have an average particle size $d_{50}$ from 1 to 80 nm.

In one embodiment the sinterable composite electrolyte compound therefore comprises, preferably contains an electrolyte selected from the group consisting of 8YSZ, 10Sc1CeSZ, 10Sc1AlSZ, 10Sc2YbSZ, 3YSZ, 6ScSZ and mixtures thereof, and one, preferably two, more preferably three, materials distributed in the electrolyte in a quantity from 0.1 to 15.0% by weight relative to the total weight of the electrolyte, wherein the material/s has/have an average particle size $d_{50}$ from 1 to 80 nm.

The sinterable composite electrolyte compound may comprise the at least one material distributed in the electrolyte in various quantities.

For example, the sinterable composite electrolyte compound preferably comprises the at least one material distributed in the electrolyte in a quantity from 2.5 to 10.0% by weight or from 4.0 to 7.5% by weight relative to the total weight of the electrolyte, if the at least one material distributed in the electrolyte is 8YSZ.

If the material distributed in the electrolyte comprises at least one material selected from the group comprising $Al_2O_3$, MgO, Al, Mg and mixtures thereof, the sinterable composite electrolyte compound comprises the at least one material that is distributed in the electrolyte preferably in a quantity von 0.2 to <2.5% by weight or from 0.3 to 1.5% by weight relative to the total weight of the electrolyte.

In one embodiment, the at least one material distributed in the electrolyte has an average particle size $d_{50}$ from 2 to 50 nm. For example, the at least one material distributed in the electrolyte has an average particle size $d_{50}$ from 2 to 10 nm or from 5 to 10 nm.

The at least one material distributed in the electrolyte in present for example in the form of nanopowder or nanofibres.

In one embodiment, the sinterable composite electrolyte compound may comprise a further material with an average particle size $d_{50}$ from 1 to 5 μm. This is particularly advantageous for improving the sintering behaviour of the composite electrolyte.

For example, the sinterable composite electrolyte compound comprises a further material with an average particle size $d_{50}$ from 1 to 3 μm or from 1.5 to 2.5 μm.

If the sinterable composite electrolyte compound comprises a further material, the further material is preferably MgO or $Al_2O_3$.

In one embodiment, the sinterable composite electrolyte compound preferably comprises the further material in a quantity from 0.1 to 1.0% by weight relative to the total weight of the electrolyte. For example, the sinterable composite electrolyte compound comprises the further material in a quantity from 0.1 to 0.8% by weight or from 0.2 to 0.8% by weight relative to that total weight of the electrolyte. The sinterable composite electrolyte compound preferably comprises the further material in a quantity from 0.3 to 0.7% by weight, or from 0.4 to 0.6% by weight relative to the total weight of the electrolyte.

Based on the advantages that the sinterable composite electrolyte compound offers, the present embodiment also relates to a sintered composite electrolyte that comprises the sinterable composite electrolyte compound as described in this document.

The sinterable composite electrolyte compound offers the advantage that it can be processed by Additive Layer Manufacturing (ALM) or non-conventional 3D manufacturing processes such as weaving technology. The sinterable composite electrolyte compound further offers the advantage that, when sintered at sintering temperatures $T_{sinter} \leq 1300°$ C. and for a bonding time $t_{bond} < 5$ h the sinterable composite electrolyte compound results in an electrolyte composite that is gas-impermeable and has a density of $\geq 5.9$ g/cm$^3$, and at the same time is capable of thin dimensioning.

Accordingly, the sintered composite electrolyte preferably has a density $\geq 5.9$ g/cm$^3$. For example, the sintered composite electrolyte preferably has a density from 6.0 g/cm$^3$ to 6.5 g/cm$^3$ or from 6.0 g/cm$^3$ to 6.3 g/cm$^3$.

A further aspect of the present embodiment relates to a method for manufacturing a sintered composite electrolyte, as described in the present document, comprising the steps of preparing a sinterable composite electrolyte compound as described herein, and sintering the sinterable composite electrolyte compound at temperatures ≤1300° C. and for a bonding time <5 h.

The sinterable composite electrolyte compound according to the embodiment may generally be prepared by mixing the electrolyte and the at least one material distributed in the electrolyte together. Sintering is carried out at temperature ≤1300° C. or from 800 to ≤1300° C., for example from 900 to ≤1300° C., preferably for a total of <5 h or for 3 to <5 h. The sintering may be carried out in a single, continuous process or in several different, chronologically separate steps. The sintering preferably takes place in a single, continuous process. In one embodiment, sintering is carried out with different temperature ramps.

A further advantage is that the sinterable composite electrolyte compound according to the embodiment has good ion-conducting capability ($O^2$) in the sintered state, and therefore can be used for a fuel cell, preferably a solid oxide fuel cell, or an exhaust gas probe or a high-temperature gas sensor (>500° C.).

Based on the advantages that the sinterable composite electrolyte offers, the present embodiment also relates to the use of the sintered composite electrolyte as described in this document in a fuel cell, preferably a solid oxide fuel cell, an exhaust gas probe or a high-temperature gas sensor.

A further aspect of the present embodiment thus relates to a fuel cell, preferably a solid oxide fuel cell, an exhaust gas probe or a high-temperature gas sensor containing the sintered composite electrolyte as described herein.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the embodiment in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the embodiment as set forth in the appended claims and their legal equivalents.

What is claimed is:

1. A sinterable composite electrolyte compound comprising:
    a) an electrolyte selected from the group consisting of 8YSZ, 10Sc1CeSZ, 10Sc1AlSZ, 10Sc2YbSZ, 3YSZ, 6ScSZ and mixtures thereof, and
    b) a material distributed in the electrolyte in a quantity from 0.1 to 15.0% by weight relative to the total weight of the electrolyte, wherein the material has an average particle size $d_{50}$ from 1 to 80 nm and comprises at least two materials selected from the group consisting of 8YSZ, $Al_2O_3$, MgO, Al, Mg, 3YSZ, 6ScSZ, 10Sc1CeSZ, 10Sc1AlSZ, 10Sc2YbSZ and mixtures thereof.

2. The sinterable composite electrolyte compound according to claim 1, wherein the sinterable composite electrolyte compound comprises the electrolyte in a quantity from 85 to 99.9% by weight, relative to the total weight of the compound.

3. The sinterable composite electrolyte compound according to claim 1, wherein the electrolyte has an average particle size $d_{50}$ from 0.5 to 5 μm and the electrolyte has a particle size $d_{80}$ of less than 5 μm.

4. The sinterable composite electrolyte compound according claim 1, wherein the electrolyte has an average particle size $d_{50}$ from 0.5 to 5 μm or the electrolyte has a particle size $d_{80}$ of less than 5 μm.

5. The sinterable composite electrolyte compound according to claim 1, wherein the material distributed in the electrolyte comprises at least three materials selected from the group consisting of 8YSZ, $Al_2O_3$, MgO, Al, Mg, 3YSZ, 6ScSZ, 10Sc1CeSZ, 10Sc1AlSZ, 10Sc2YbSZ and mixtures thereof.

6. The sinterable composite electrolyte compound according to claim 1, wherein the sinterable composite electrolyte compound comprises the material distributed in the electrolyte in a quantity from 0.2 to 10.0% by weight relative to the total weight of the electrolyte.

7. The sinterable composite electrolyte compound according to claim 1, wherein the material distributed in the electrolyte has an average particle size $d_{50}$ from 2 to 50 nm.

8. The sinterable composite electrolyte compound according to claim 1, wherein the material distributed in the electrolyte is present in the form of nanopowder or nanofibres.

9. The sinterable composite electrolyte compound according to claim 1, wherein the sinterable composite electrolyte compound additionally comprises a further material having an average particle size $d_{50}$ from 1 to 5 μm.

10. The sinterable composite electrolyte compound according to claim 9, wherein the sinterable composite electrolyte compound comprises the further material in a quantity from 0.1 to 1.0% by weight relative to the total weight of the electrolyte.

11. A sintered composite electrolyte comprising the sinterable composite electrolyte compound according to claim 1.

12. A method for manufacturing a sintered composite electrolyte having a density greater than or equal to 5.9 g/cm$^3$, comprising the steps of:
    preparing a sinterable composite electrolyte compound comprised of an electrolyte selected from the group consisting of 8YSZ, 10Sc1CeSZ, 10Sc1AlSZ, 10Sc2YbSZ, 3YSZ, 6ScSZ and mixtures thereof, and a material distributed in the electrolyte in a quantity from 0.1 to 15.0% by weight relative to the total weight of the electrolyte, wherein the material has an average particle size $d_{50}$ from 1 to 80 nm and comprises at least two materials selected from the group consisting of 8YSZ, $Al_2O_3$, MgO, Al, Mg, 3YSZ, 6ScSZ, 10Sc1CeSZ, 10Sc1AlSZ, 10Sc2YbSZ and mixtures thereof,
    sintering the sinterable composite electrolyte compound at temperatures less than or equal to 1300° C. and for a bonding time less than 5 hours.

13. A fuel cell, exhaust gas probe or high-temperature gas sensor containing a sintered composite electrolyte wherein the sintered composite electrolyte has a density greater than or equal to 5.9 g/cm$^3$ and comprises a sinterable composite electrolyte compound comprising:
    a) an electrolyte selected from the group consisting of 8YSZ, 10Sc1CeSZ, 10Sc1AlSZ, 10Sc2YbSZ, 3YSZ, 6ScSZ and mixtures thereof, and
    b) a material distributed in the electrolyte in a quantity from 0.1 to 15.0% by weight relative to the total weight of the electrolyte, wherein the material has an average particle size $d_{50}$ from 1 to 80 nm and comprises at least two materials selected from the group consisting of 8YSZ, Al₂O₃, MgO, Al, Mg, 3YSZ, 6ScSZ, 10Sc1CeSZ, 10Sc1AlSZ, 10Sc2YbSZ, and mixtures thereof.

14. The sintered composite electrolyte according to claim 11, wherein the sintered composite electrolyte has a density greater than or equal to 5.9 g/cm³.

* * * * *